United States Patent [19]

Kanemaru et al.

[11] Patent Number: 5,049,464
[45] Date of Patent: Sep. 17, 1991

[54] PHOTOSENSITIVE MEMBER FOR ELECTROPHOTOGRAPHY

[75] Inventors: Tetsuro Kanemaru, Tokyo; Toshihiro Kikuchi; Akihiro Senoo, both of Yokohama; Ryoji Yashiro, Yamanashi, all of Japan

[73] Assignee: Canon Kabushiki Kaisha, Tokyo, Japan

[21] Appl. No.: 458,459

[22] Filed: Dec. 28, 1989

[30] Foreign Application Priority Data

Dec. 29, 1988 [JP] Japan ................. 63-330983

[51] Int. Cl.$^5$ .................... G03G 5/06; G03G 5/14
[52] U.S. Cl. .................... 430/59; 252/500
[58] Field of Search .................... 430/59

[56] References Cited

U.S. PATENT DOCUMENTS

| | | | |
|---|---|---|---|
| 3,554,745 | 1/1971 | Van Allen | 96/1.6 |
| 3,567,438 | 3/1971 | Brooker | 96/1.6 |
| 3,586,500 | 1/1971 | Contois | 96/1.6 |
| 3,684,502 | 8/1972 | Granza | 96/1.6 |
| 3,857,851 | 9/1974 | Shattuck et al. | 96/1.5 |
| 4,150,987 | 4/1979 | Anderson et al. | 96/1.5 |
| 4,390,611 | 6/1983 | Ishikawa et al. | 430/59 |
| 4,869,988 | 9/1989 | Ong et al. | 430/59 |

FOREIGN PATENT DOCUMENTS

| | | |
|---|---|---|
| 161934 | 11/1985 | European Pat. Off. |
| 271355 | 11/1973 | Japan |
| 094828 | 8/1976 | Japan |
| 118035 | 8/1979 | Japan |
| 058445 | 11/1979 | Japan |
| 151955 | 11/1979 | Japan |
| 052063 | 4/1980 | Japan |
| 195245 | 11/1982 | Japan |
| 195254 | 11/1982 | Japan |
| 198043 | 11/1983 | Japan |
| 023162 | 1/1988 | Japan |
| 058451 | 3/1988 | Japan |

Primary Examiner—David Welsh
Attorney, Agent, or Firm—Fitzpatrick, Cella, Harper & Scinto

[57] ABSTRACT

A photosensitive member for electrophotography, including an electroconductive substrate and a photosensitive layer disposed thereon, wherein the photosensitive layer comprises a substituted amino compound represented by the following general formula (I):

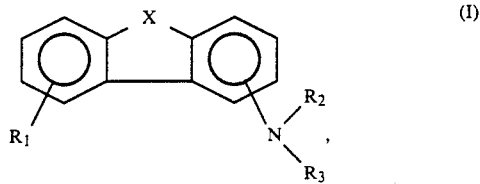

wherein X denotes —O—, —S—, or

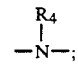

$R_1$ denotes a hydrogen atom, alkyl, alkoxyl or halogen atom; and $R_2$, $R_3$ and $R_4$ respectively denote an alkyl, aralkyl, aryl or heterocyclic group.

11 Claims, No Drawings

PHOTOSENSITIVE MEMBER FOR ELECTROPHOTOGRAPHY

FIELD OF THE INVENTION AND RELATED ART

The present invention relates to a photosensitive member for electrophotography, particularly to a photosensitive member for electrophotography comprising a low-molecular weight organic photoconductor capable of providing improved electrophotographic characteristics.

Hitherto, there have been proposed a large number of organic photoconductive polymers to be used for electrophotographic photosensitive members such as polyvinyl carbazole. These conventional organic polymers are superior to inorganic photoconductive materials in lightness (in weight), film-forming property, etc., but are inferior to the latter in sensitivity, durability, stability to environmental change, mechanical strength, etc.

On the other hand, there have been proposed several low-molecular weight organic photoconductive materials such as hydrazone compound (U.S. Pat. No. 4,150,987), triaryl pyrazoline compound (U.S. Pat. No. 3,837,851), and 9-styryl anthracene (Japanese Laid-Open Patent Application (JP-A, KOKAI) Nos. 94828/1976 and 94829/1976).

In a case where the conventional low-molecular weight organic photoconductors represented by those a described above are used, the above-mentioned defect in film-forming property, which has conventionally posed a problem in the field of the organic photoconductive polymer, may be obviated by appropriately selecting a binder to be used in combination therewith. However, these conventional organic photoconductors can not provide a sufficient sensitivity.

Based on such a viewpoint, there has recently been proposed a laminate-type structure wherein the photosensitive layer is function-separated into a charge generation layer and a charge transport layer. The electrophotographic photosensitive member comprising such a photosensitive layer may be improved in sensitivity to visible light, charge retentivity, surface strength, etc.

As the charge-transporting substance constituting the above-mentioned charge transport layer, a large number of organic compounds have heretofore been proposed. Examples thereof include: pyrazoline compounds (Japanese Laid-Open Patent Application No. 72231/1977), hydrazone compounds (U.S. Pat. No. 842,431 and Japanese Laid-Open Patent Application No. 52063/1980), triphenylamine compounds (Japanese Laid-Open Patent Application Nos. 195254/1982 and 58445/1979), stilbene compounds (Japanese Laid-Open Patent Application Nos. 151955/1979 and 198043/1983), carbazole compounds (Japanese Laid-Open Patent Application Nos. 150128/1979 and 58451/1988), benzothiophene compounds (Japanese Laid-Open Patent Application No. 110835/1979), etc.

However, in the electrophotographic photosensitive member using the conventional low-molecular weight organic compound as the charge-transporting substance, the sensitivity and other electrophotographic characteristics are not necessarily sufficient, and the light part potential and dark part potential are liable to show a considerable change, when charging and exposure operations are conducted repetitively.

Accordingly, with respect to such an electrophotographic photosensitive member, there is still room for improvement.

SUMMARY OF THE INVENTION

An object of the present invention is to provide an electrophotographic photosensitive member which has solved the above-mentioned various problems encountered in the conventional photosensitive member.

Another object of the present invention is to provide an electrophotographic photosensitive member using a novel organic photoconductor which may easily be produced, is relatively inexpensive and is excellent in durability.

According to the present invention, there is provided a photosensitive member for electrophotography, comprising an electroconductive substrate and a photosensitive layer disposed thereon, wherein the photosensitive layer comprises a substituted amino compound represented by the following general formula (I):

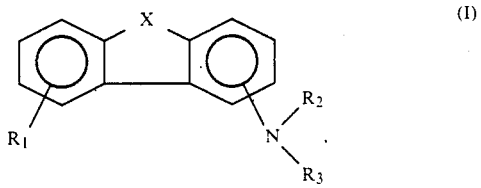

wherein X denotes —O—, —S—, or

denotes a hydrogen atom, alkyl, alkoxyl or halogen atom; and $R_2$, $R_3$ and $R_4$ respectively denote an alkyl, aralkyl, aryl or heterocyclic group.

These and other objects, features and advantages of the present invention will become more apparent upon a consideration of the following description of the preferred embodiments of the present invention.

DETAILED DESCRIPTION OF THE INVENTION

In the above general formula (I), specific examples of the alkyl group may include methyl, ethyl and n-propyl groups; specific examples of the alkoxy group may include methoxy and ethoxy group; specific examples of the halogen atom may include fluorine, chlorine and bromine atoms; specific examples of the aralkyl group may include benzyl and phenethyl groups; specific examples of the aryl group may include benzene, naphthalene, anthracene and biphenyl rings; and specific examples of the heterocyclic group may include pyridine, quinoline, and thiophene rings. These alkyl, alkoxyl, aralkyl, aryl and heterocyclic groups can also have a substituent such as alkyl and alkoxy groups preferably of about $C_1$ to $C_3$.

Representative examples of the compound represented by the above-mentioned formula (I) are described hereinbelow. However, the compound represented by the general formula (I) usable in the present invention is not restricted to these specific examples.

<Compound Examples>
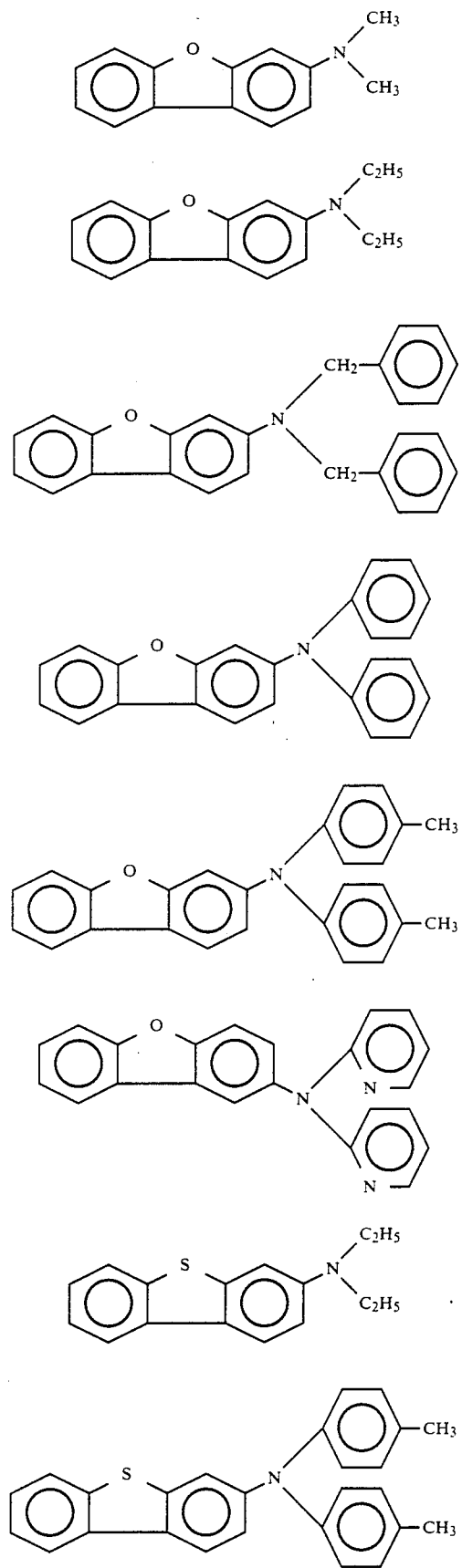
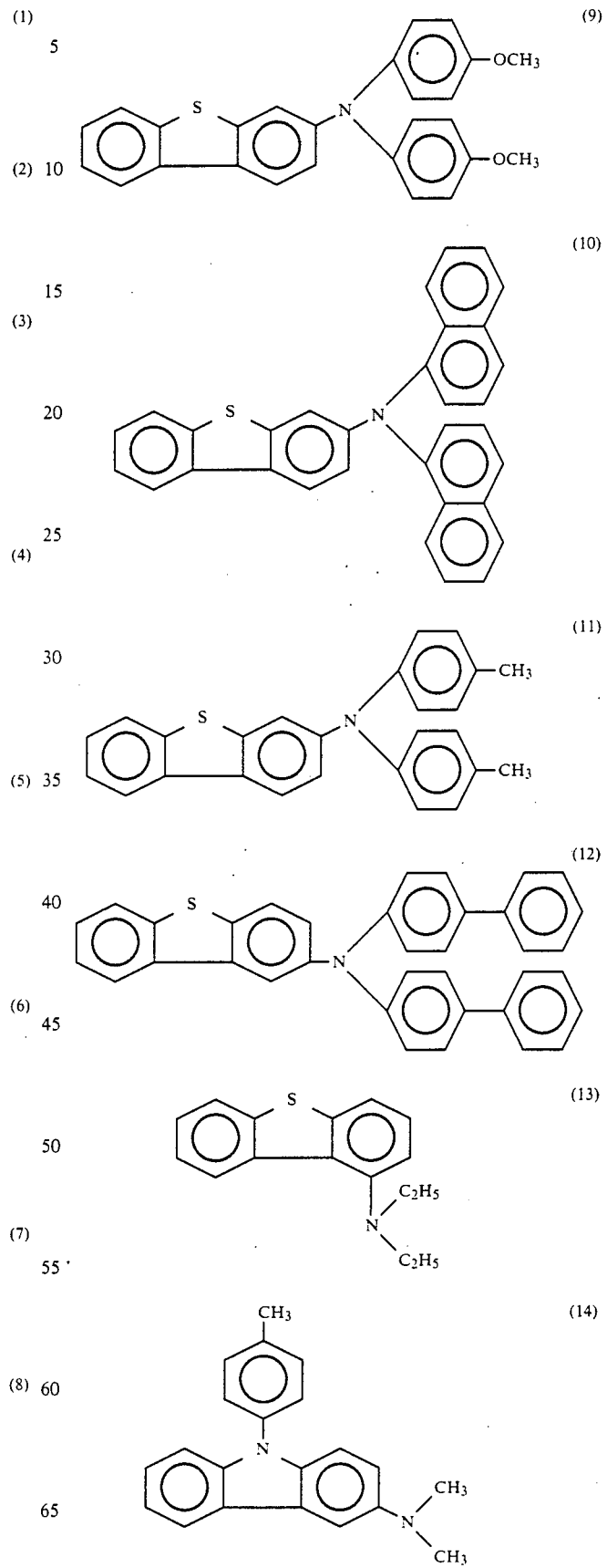

-continued
<Compound Examples>
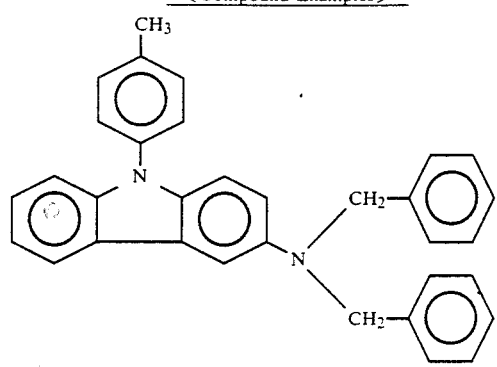 (15)
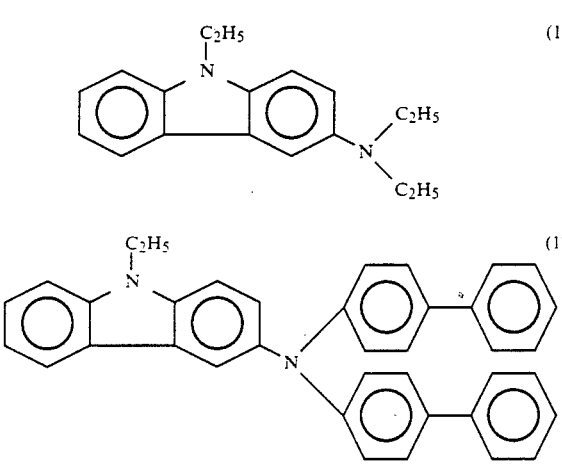 (16)
(17)
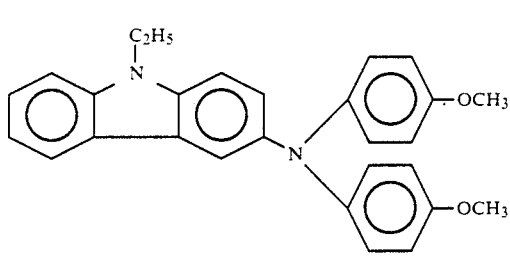 (18)
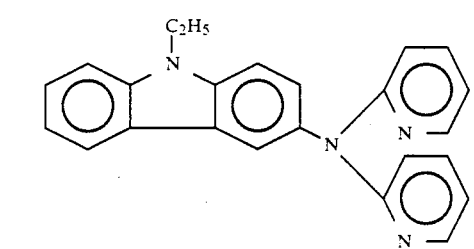 (19)
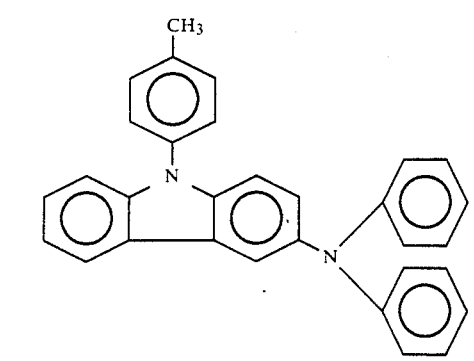 (20)
-continued
<Compound Examples>
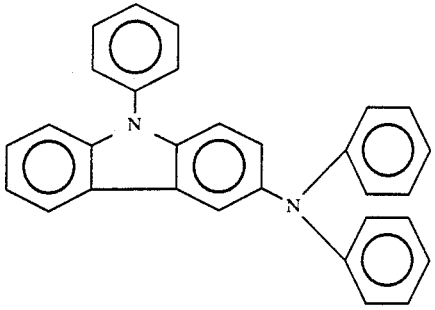 (21)
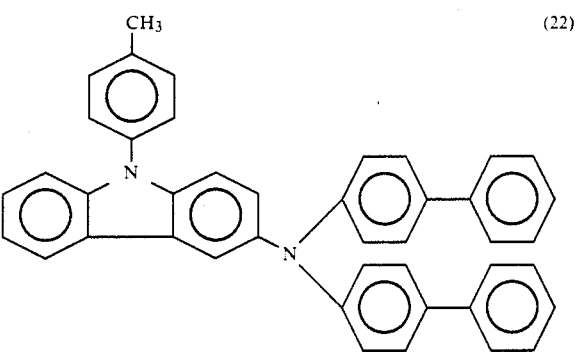 (22)
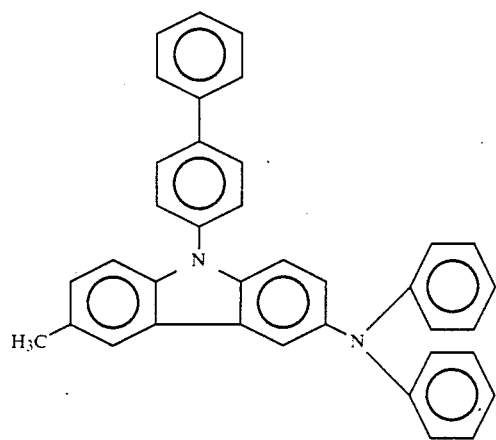 (23)
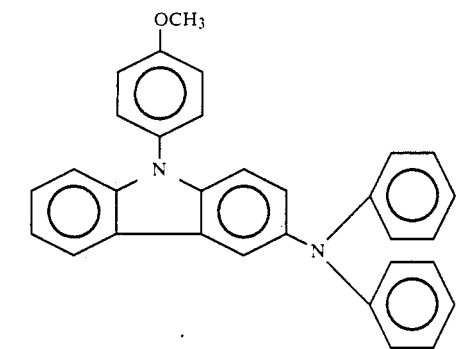 (24)
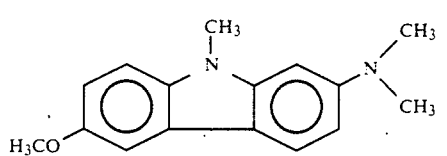 (25)

-continued
<Compound Examples>

(26)
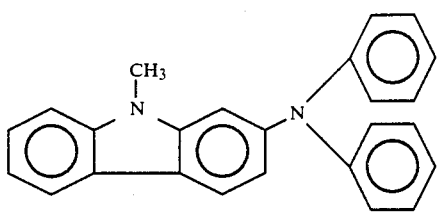

(27)
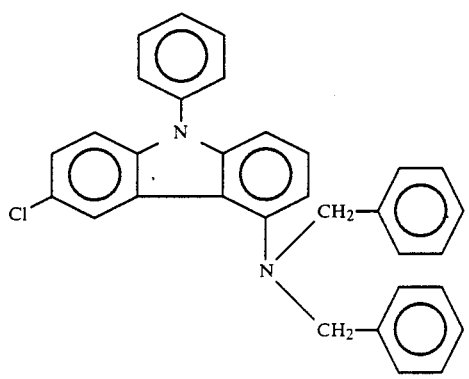

(28)
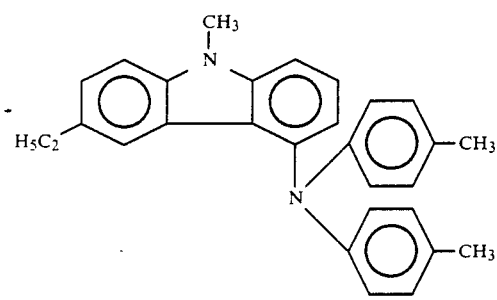

The above-mentioned Compound Examples may be synthesized in the following manner.

Synthesis of Compound Example No. 5

4.00 g (21.86 mmol) of 3-aminodibenzofuran, 14.29 g (65.57 mmol) of p-iodotoluene, 24.13 g (174.9 mmol) of anhydrous potassium carbonate, 4.00 g of copper powder and 75 cc of nitrobenzene were charged in a 300 ml-flask and were refluxed for four hours under heating by using a mantle heater thereby to react such a mixture. After the completion of the reaction, the reaction mixture was subjected to filtration, the nitrobenzene was removed from the resultant filtrate by distillation under reduced pressure, and methanol was added to the residue to cause crystallization. The resultant crystals were washed with methanol, and were subjected to separation to be purified by using a silica gel column thereby to obtain 5.05 g of the above-mentioned Compound Example No. 5 (yield=63.6 %).

|  | Elemental analysis | | |
| --- | --- | --- | --- |
|  | C (%) | H (%) | N (%) |
| Calculated value | 85.95 | 5.79 | 3.86 |
| Observed value | 85.99 | 5.70 | 3.89 |

As described above, the charge-transporting substance according to the present invention may easily be synthesized inexpensively. The other compounds according to the present invention may be synthesized in a similar manner as described in the above Synthesis Example.

In a preferred embodiment of the present invention, the photosensitive layer is function-separated into a charge generation layer and a charge transport layer, and the charge transport layer comprises the compound represented by the above-mentioned general formula (I) as a charge-transporting substance.

The charge transport layer according to the present invention may preferably be formed by dissolving the above-mentioned compound of the formula (I) in an appropriate solvent together with a binder, applying the resultant coating liquid such as solution onto a predetermined surface, and the drying the resultant coating.

Examples of the binder to be used for forming the charge transport layer may include: polyarylate resins, polysulfone resins, polyamide resins, acrylic resins, acrylonitrile resins, methacrylic resins, vinyl chloride resins, vinyl acetate resins, phenol resins, epoxy resins, polyester resins, alkyd resins, polycarbonate polyurethane, or copolymer resins containing two or more of the recurring units of these resins, such as styrene-butadiene copolymers, styrene-acrylonitrile copolymers, styrene-maelic acid copolymers, etc. Also, other than such insulating polymers, organic photoconductive polymers such as polyvinylcarbazole, polyvinylanthracene and polyvinylpyrene may be used.

In the charge transport layer, the charge-transporting substance may preferably be used in an amount of 10–500 wt. parts, more preferably 50–200 wt. parts, per 100 wt. parts of the binder.

The charge transport layer is electrically connected to the charge generation layer as described hereinafter, and has a function of receiving charge carriers injected from the charge generation layer in the presence of an electric field and of transporting these charge carriers to the surface of the charge transport layer. In such an embodiment, the charge transport layer may be disposed on the charge generation layer, or may be disposed under the charge generation layer. The charge transport layer may preferably be disposed on the charge generation layer. It is not preferred that the charge transport layer has too large a thickness, since there is a certain limit to the thickness thereof suitable for the transport of the charge carriers. In general, the charge transport layer may preferably have a thickness of 5–40 microns, more preferably 10–30 microns.

The organic solvent to be used in the above-mentioned formation of the charge transport layer may vary depending on the kind of the binder used therefor, and may preferably be selected from those which do not substantially dissolve the charge generation layer or a primer (or undercoat layer) as described hereinafter.

Specific examples of such an organic solvent may include: alcohols such as methanol, ethanol, and isopropanol; ketones such as acetone, methyl ethyl ketone, and cyclohexanone; amides such as N,N-dimethylformamide and N,N-dimethylacetamide; sulfoxides such as dimethyl sulfoxide; ethers such as tetrahydrofuran, dioxane, and ethylene glycol monomethyl ether; esters such as methyl acetate and ethyl acetate; aliphatic halogenated hydrocarbons such as chloroform, methylene chloride, dichloroethylene, carbon tetrachloride, and trichloroethylene; aromatic compounds such as benzene, toluene, xylene, monochlorobenzene, and dichlorobenzene; etc.

The coating may be effected by various coating methods such as dip coating, spray coating, wire bar coating, and blade coating. The drying should preferably be conducted in the sequence of drying at room temperature to a "tack-free" state and then heat drying. In general, the heat drying may preferably be conducted for a time in the range of 5 minutes to 2 hours at a temperature of 30° C. to 200° C. under quiescent condition or under blowing.

The charge transport layer according to the present invention can further contain an additive selected from various species thereof. Examples of such an additive may include: plasticizers such as diphenyl, m-terphenyl and dibutyl phthalates; surface-lubricating agents such as silicone oil, graft-type silicone polymers, and various fluorocarbons; potential stabilizing agents such as dicyanovinyl compounds and carbazole derivatives; anti-oxidizing agents such as β-carotene, Ni complexes, and 1,4-diazabicyclo[2,2,2]octane; etc.

The charge generation layer may comprise a charge-generating substance. Specific examples of the charge-generating substance may include: inorganic charge-generating substances such as selenium, selenium-tellurium, and amorphous silicon; and organic charge-generating substances including: cationic dyes such as pyrylium dye, thiapyrylium dye, azulenium dye, thiacyamine dye, and quinocyanine dye; polycyclic quinone pigments such as squarium salt dye, phthalocyanine pigment, anthanthrone pigment, dibenzpyrenequinone pigment, and pyranthrone pigment; indigo pigment; quinacridone pigment; azo pigment; etc. These charge-generating substances may be used singly or as a combination of two or more species. The charge generation layer may be formed by using such a charge-generating substance in the form of a vapor deposition layer or coating layer.

Among the above-mentioned charge-generating substances, the azo pigment particularly includes various types. Representative structures of the azo pigment preferably used in the present invention are described hereinbelow. When the azo pigment is represented by a general formula including the following central skeleton A:

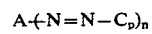

wherein Cp denotes a coupler portion (or coupler moiety) and n is 2 or 3, specific examples of the central skeleton A include those comprising the following structures:

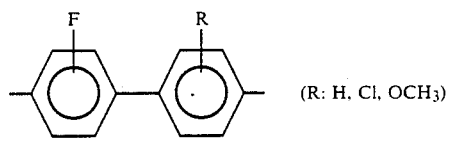  A-1

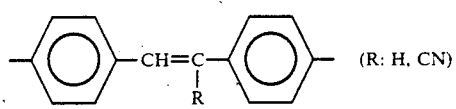  A-2

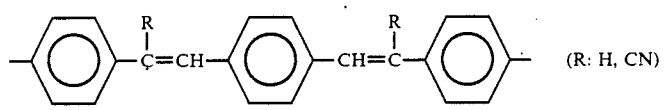  A-3

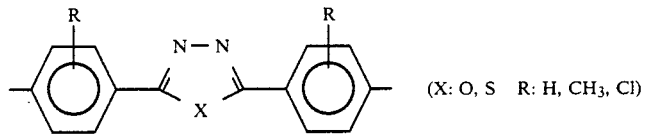  A-4

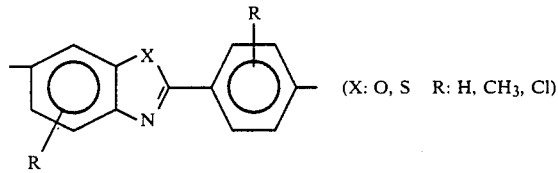  A-5

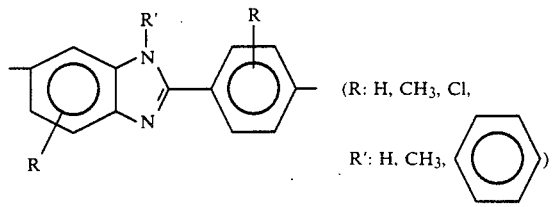  A-6

-continued
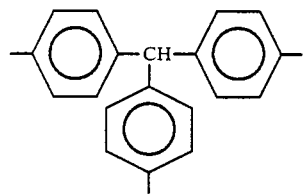
A-7
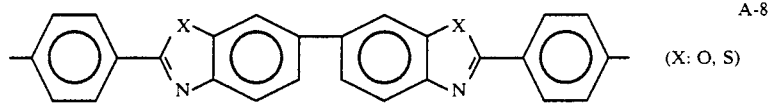
A-8 (X: O, S)
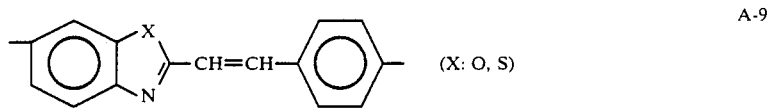
A-9 (X: O, S)
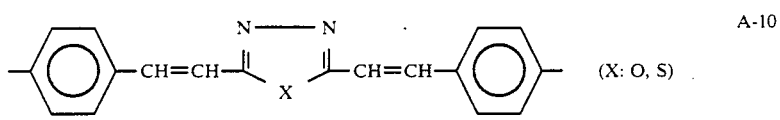
A-10 (X: O, S)
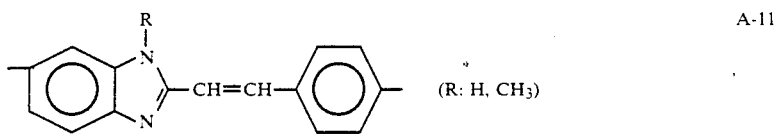
A-11 (R: H, CH₃)
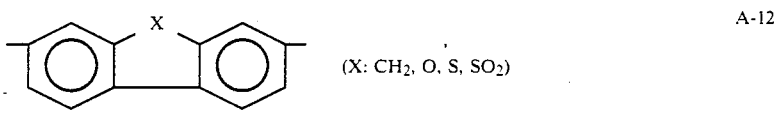
A-12 (X: CH₂, O, S, SO₂)
A-13
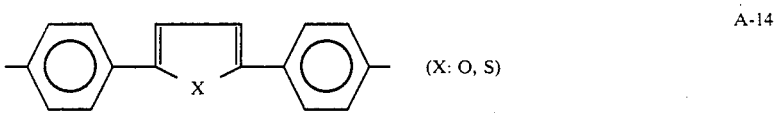
A-14 (X: O, S)
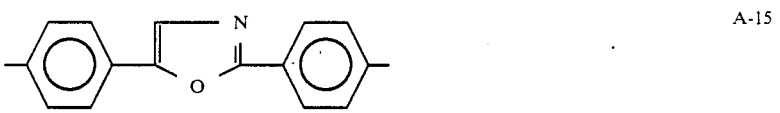
A-15
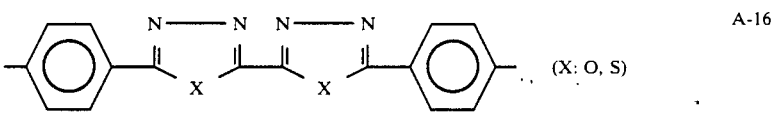
A-16 (X: O, S)
A-17
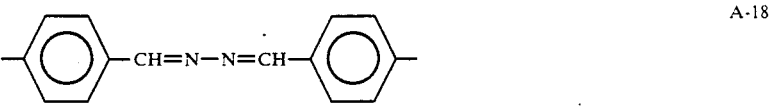
A-18

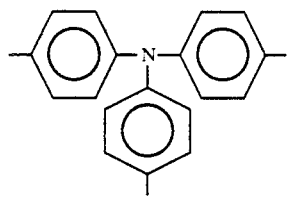 A-19
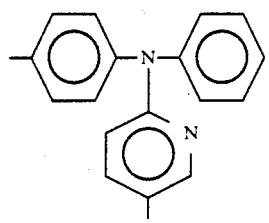 A-20
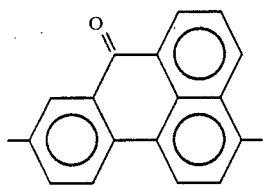 A-21
(R: H, CH₃)
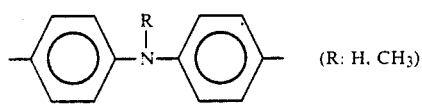 A-22
Specific examples of the coupler portion Cp include those having the following structures;
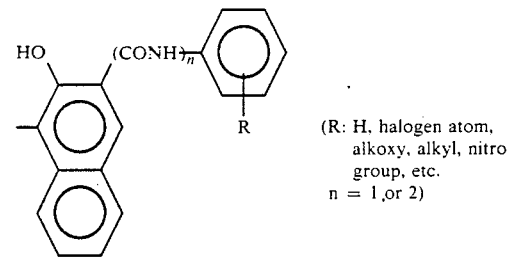 Cp-1
(R: H, halogen atom, alkoxy, alkyl, nitro group, etc.
n = 1,or 2)
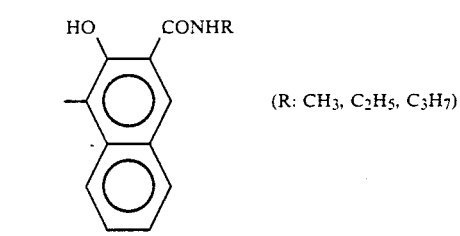 Cp-2
(R: CH₃, C₂H₅, C₃H₇)
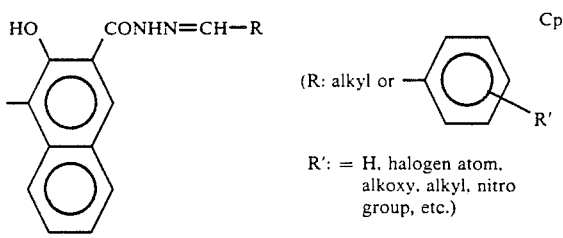 Cp-3
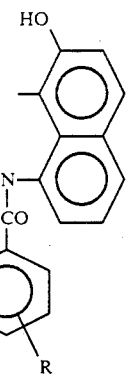
(R: alkyl or
R': = H, halogen atom, alkoxy, alkyl, nitro group, etc.)
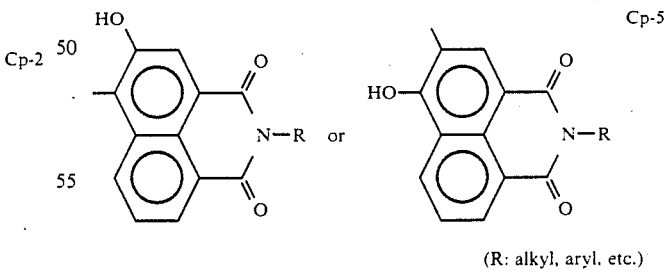 Cp-4
(R: H, halogen atom, alkoxyl, alkyl, nitro group, etc.)
Cp-5
(R: alkyl, aryl, etc.)
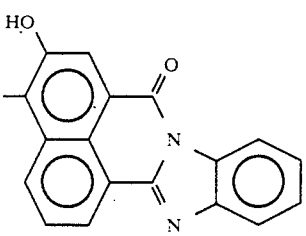 Cp-6
or

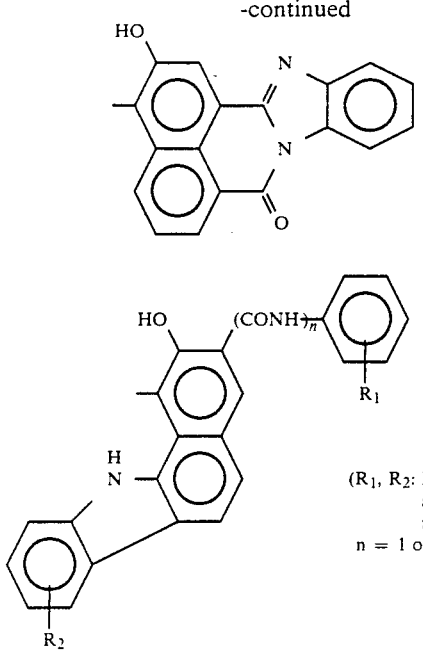

Cp-7

(R₁, R₂: H, halogen atom, alkoxy, alkyl, nitro group, etc.
n = 1 or 2)

The above-mentioned central structure A and coupler Cp may appropriately be combined to form a pigment as a charge-generating substance.

The charge generation layer may be formed by vapor-depositing such a charge-generating substance by means of a vacuum vapor deposition device, or by applying a dispersion containing such a charge-generating substance dispersed therein, together with an appropriate binder as desired.

The binder to be used for forming the charge generation layer may be selected from a wide variety of insulating resins or alternatively from organic photoconductive polymers such as poly-N-vinylcarbazole, polyvinylanthracene, and polyvinylpyrene. There may preferably be used the insulating resin such as polyvinyl butyral, polyarylates (e.g., polycondensation product between bisphenol A and phthalic acid), polycarbonate, polyester, phenoxy resin, acrylic resin, polyacrylamide resin, polyamide, polyvinyl pyridine, cellulose resin, urethane resin, epoxy resin, casein, polyvinyl alcohol, and polyvinyl pyrrolidone.

The resin may preferably be contained in the charge generation layer in an amount of 5-80 wt. %, more preferably 10-40 wt. %.

Specific examples of the organic solvent usable in the coating of the charge generation layer may include: alcohols such as methanol, ethanol, and isopropanol; ketones such as acetone, methyl ethyl ketone, and cyclohexanone; amides such as N,N-dimethylformamide and N,N-dimethylacetamide; sulfoxides such as dimethyl sulfoxide; ethers such as tetrahydrofuran, dioxane, and ethylene glycol monomethyl ether; esters such as methyl acetate and ethyl acetate; aliphatic halogenated hydrocarbons such as chloroform, methylene chloride, dichloroethylene, carbon tetrachloride, and trichloroethylene; aromatic compounds such as benzene, toluene, xylene, monochlorobenzene, and dichlorobenzene; etc.

The charge generation layer may preferably contain the above-mentioned charge-generating substance in an amount as large as possible, so that it may to provide a sufficient absorbance. Further, the charge generation layer may preferably be a thin layer having a thickness of 5 microns or below, more preferably 0.01 -1 micron so that it may inject charge carriers generated therein into the charge transport layer within the lifetime of the charge carriers. This may be attributable to facts such that most of the incident light quantity may preferably be absorbed into the charge generation layer to generate a large number of charge carriers, and that the thus generated charge carriers may preferably be injected into the charge transport layer without deactivation due to recombination or trapping thereof.

The above-mentioned photosensitive layer having a laminate structure comprising a charge generation layer and a charge transport layer may be disposed on an electroconductive substrate.

The electroconductive substrate may be a substrate which per se has an electroconductivity such as those of aluminum, aluminum alloy, copper, zinc, and stainless steel; alternatively, the above-mentioned metal substrate or a substrate of a plastic coated with, e.g., a vacuum vapor-deposited layer of aluminum, aluminum alloy, indium oxide, tin oxide or indium oxide-tin oxide alloy, or a mixture of an electroconductive powder (such as aluminum powder, titanium oxide, tin oxide, zinc oxide, carbon black and silver particles) and an appropriate binder; a substrate of paper or plastic impregnated with electroconductive particles, or a plastic substrate coated with an electroconductive polymer layer. The electroconductive substrate may be in any form such as sheet, drum, etc.

Between the electroconductive substrate and the photosensitive layer, there can be formed a primer or undercoat layer having a barrier function and an adhesive function. The primer layer may comprise, e.g., casein, polyvinyl alcohol, nitrocellulose, ethylene-acrylic acid copolymer, polyamide (e.g., nylon 6, nylon 66, nylon 610, copolymer nylon, alkoxymethylated nylon, etc.), polyurethane, gelatin, or aluminum oxide. The thickness of the primer layer should preferably be 0.1-5 microns, particularly 0.5 to 3 microns.

In the electrophotographic photosensitive member according to the present invention, a protective layer can further be disposed on the photosensitive layer. Such a protective layer may comprise a resin, or a resin and an electroconductive material dispersed therein.

In another embodiment of the present invention, a pigment or dye having a photoconductivity may be used as a sensitizer. Examples of such a dye or pigment include: the above-mentioned disazo pigment, pyrylium dye, thiapyrylium dye, selenapyrylium dye, benzopyrylium dye, benzothiapyrylium dye, naphthopyrylium dye, and naphthothiapyrylium dye, as described in U.S. Pat. Nos. 3,554,745; 3,567,438; and 3,586,500.

In a still another embodiment of the present invention, an eutectic (crystal) complex comprising a pyrylium dye (as disclosed in U.S. Pat. No. 3,684,502) and an electrically insulating polymer comprising an alkylidene-diarylene portion may be used as a sensitizer. Such an eutectic complex may be formed by dissolving 4-[4-bis(2-chloroethyl)aminophenyl]-2,6-diphenyl-thiapyrylium perchlorate and poly(4,4'-isopropylidene diphenylene carbonate) in a halogenated hydrocarbon-type solvent (e.g., dichloromethane, chloroform, carbon tetrachloride, 1,1-dichloroethane, 1,2-dichloroethane, 1,1,2-trichloroethane, chlorobenzene, bromobenzene, 1,2-dichlorobenzene, etc.), and then adding a nonpolar solvent (e.g., hexane, octane, decane, 2,2,4-trimethylbenzene, ligroin, etc.) to the resultant mixture so as to produce a particulate eutectic complex. In such an embodiment, the electrophotographic photosensitive member may include a binder such as styrene-butadiene copolymer, silicone resin, vinyl resin, vinylidene chloride-acrylonitrile copolymer, styrene-acrylonitrile copolymer, vinyl acetate-vinyl chloride copolymer, polyvinyl butyral, polymethyl methacrylate, poly-N-butyl methacrylate, polyester, cellulose ester, etc.

The electrophotographic photosensitive member according to the present invention may be used not only for ordinary copying machines but also in the fields related to the electrophotography such as laser printers, CRT printers and electrophotographic plate-making.

The present invention will be described in more detail with reference to Examples.

EXAMPLE 1

5 g of a disazo pigment represented by the following formula:

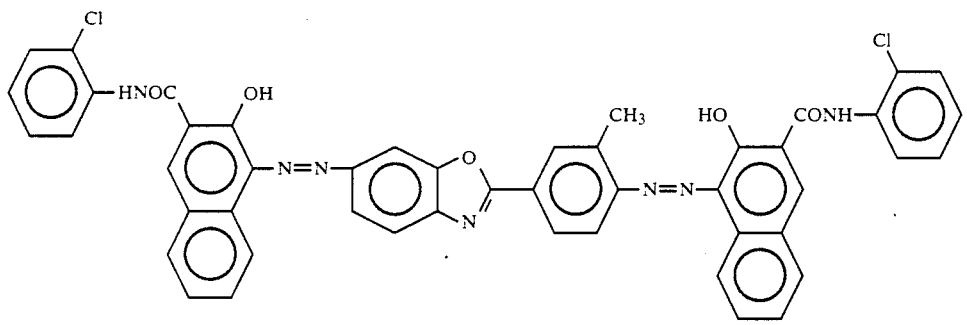

and a solution obtained by dissolving 2 g of a butyral resin (butyral degree: 63 mol. %) in 100 ml of cyclohexanone were dispersed for 24 hours by means of a sand mill to prepare a coating liquid. The thus prepared coating liquid was applied onto an aluminum sheet by means of a wire bar to form a charge generation layer having a thickness (after drying) of 0.2 micron.

Then, 10 g of the above-mentioned Compound Example No. 16 and 10 g of a polycarbonate resin (weight-average molecular weight = 20,000) were dissolved in 70 g of monochlorobenzene to prepare a coating liquid. The coating liquid was applied onto the above-mentioned charge generation layer by means of a wire bar to form a charge transport layer having a thickness (after drying) of 20 microns, whereby an electrophotographic photosensitive member having a laminate structure was prepared.

The thus prepared photosensitive member was charged by using corona (−5 KV) according to a static method by means of an electrostatic copying paper tester (Model: SP-428, mfd by Kawaguchi Denki K. K.) and retained in a dark place for 1 sec. Thereafter, the photosensitive member was exposed to light at an illuminance of 20 lux, to evaluate the charging characteristic. In order to evaluate the charging characteristic, the surface potential ($V_0$), the potential ($V_1$) obtained after a dark decay of 1 sec, and the exposure quantity ($E_{\frac{1}{2}}$) required for decreasing the potential $V_1$ to ½ thereof were measured.

Further, in order to measure the variations in light part potential and dark part potential in repetitive use, the photosensitive member prepared in this instance was bonded to the cylinder for a photosensitive drum to be used for a plain paper copying (PPC) machine (NP-3525, mfd. by Canon K. K.) and subjected to a copying test of 5000 sheets, and thereafter, the light part potential (VL) and dark part potential (VD) were measured in the initial stage and after the copying of 5000 sheets to evaluate variations therein. The initial VD and VL were set to −700 V and −200 V, respectively.

The results are shown in the following Table 1.

TABLE 1

| | $V_0$ (V) | $V_1$ (V) | $E_{\frac{1}{2}}$ (lux·sec) | Initial potential (V) | | Potential after copying of 5000 sheets (V) |
|---|---|---|---|---|---|---|
| Example 1 | −735 | −712 | 1.2 | $V_D$ | −700 | −687 |
| | | | | $V_L$ | −200 | −219 |

EXAMPLES 2-10, COMPARATIVE EXAMPLES 1-3

Nine species of photosensitive members were prepared in the same manner as in Example 1 except that the above-mentioned Compound Examples (3), (8), (9), (12), (14), (15), (20), (21) and (23) were respectively used as the charge-transporting substance instead of the Compound Example (16), and that a pigment having the following formula was used as the charge-generating substance (Examples 2-10).

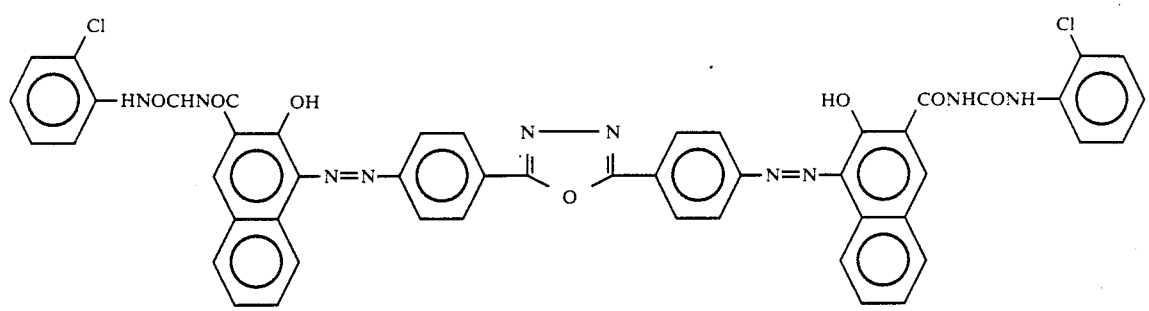

The electrophotographic characteristic of the thus obtained photosensitive members were measured in the same manner as in Example 1.

Further, for the purpose of comparison, three species of photosensitive members were prepared in the same manner as in Example 1 except that the following comparative compounds were respectively used as the charge-transporting substance (Comparative Examples 1-3).

The electrophotographic characteristic of the thus obtained photosensitive members were measured in the same manner as in Example 1.

The results are shown in the following Tables 2 and 3.

-continued
Comparative Compounds

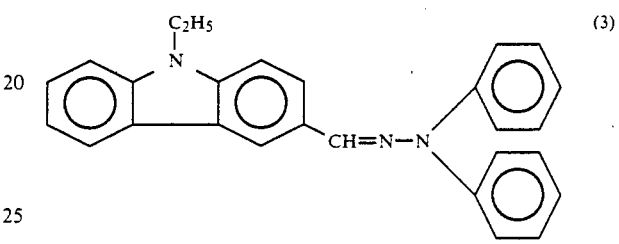
(3)

TABLE 2

| Example | Compound Example | $V_0$ (V) | $V_1$ (V) | $E_{\frac{1}{2}}$ (lux·sec) | Initial potential $V_D$(V) | Initial potential $V_L$(V) | Potential after copying of 5000 sheets $V_D$(V) | Potential after copying of 5000 sheets $V_L$(V) |
|---|---|---|---|---|---|---|---|---|
| 2 | (3) | −715 | −702 | 2.3 | −700 | −200 | −685 | −235 |
| 3 | (8) | −705 | −701 | 1.1 | −700 | −200 | −681 | −214 |
| 4 | (9) | −721 | −718 | 1.3 | −700 | −200 | −689 | −218 |
| 5 | (12) | −709 | −701 | 1.2 | −700 | −200 | −685 | −209 |
| 6 | (14) | −695 | −686 | 2.5 | −700 | −200 | −690 | −233 |
| 7 | (15) | −699 | −681 | 1.8 | −700 | −200 | −693 | −240 |
| 8 | (20) | −734 | −721 | 0.9 | −700 | −200 | −692 | −204 |
| 9 | (21) | −710 | −695 | 0.8 | −700 | −200 | −684 | −212 |
| 10 | (23) | −685 | −681 | 0.9 | −700 | −200 | −689 | −224 |

TABLE 3

| Comp. Example | Comparative Compounds | $V_0$ (V) | $V_1$ (V) | $E_{\frac{1}{2}}$ (lux·sec) | Initial potential $V_D$(V) | Initial potential $V_L$(V) | Potential after copying of 5000 sheets $V_D$(V) | Potential after copying of 5000 sheets $V_L$(V) |
|---|---|---|---|---|---|---|---|---|
| 1 | 1 | −700 | −695 | 5.2 | −700 | −200 | 612 | 262 |
| 2 | 2 | −701 | −695 | 6.1 | −700 | −200 | −670 | −310 |
| 3 | 3 | −700 | −691 | 2.9 | −700 | −200 | −640 | −287 |

As apparent from Tables 1-3, the photosensitive member using the compound according to the present invention showed a better sensitivity and less potential variations in successive copying, as compared with those of Comparative Examples.

EXAMPLE 11

A coating liquid obtained by dissolving 5 g of a methoxymethylated nylon resin (number-average molecular weight = 32,000) and 10 g of an alcohol-soluble copolymer nylon resin (number-average molecular weight = 29,000) in 95 g of methanol was applied onto an aluminum substrate by means of a wire bar to form a primer layer having a thickness of 1 micron (after drying).

Then, 10 g of a charge-generating substance represented by the following formula:

Comparative Compounds
(1)
(2)

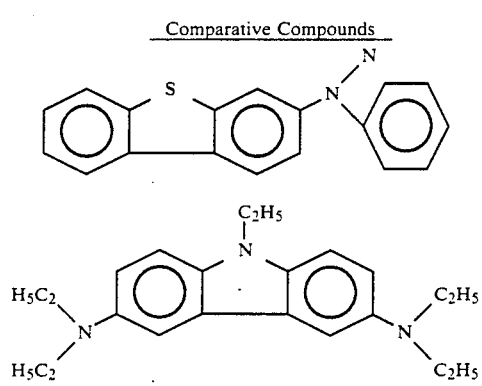

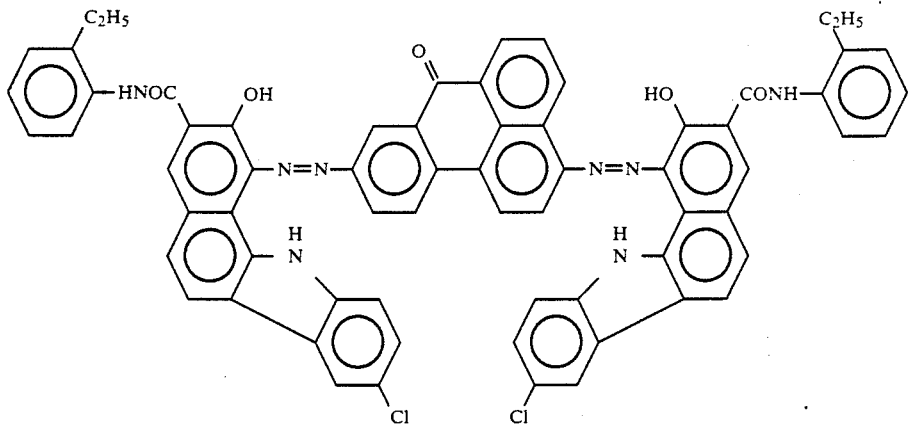

a solution obtained by dissolving 5 g of a butyral resin (butyral degree: 63 mol. %) and 200 g of dioxane were dispersed for 48 hours by means of a ball mill disperser to prepare a coating liquid. The thus prepared coating liquid was applied onto the above-mentioned primer layer by a blade coating method to form a charge generation layer having a thickness (after drying) of 0.15 micron.

Then, 10 g of the above-mentioned Compound Example No. 22 and 10 g of a polymethyl methacrylate resin (weight-average molecular weight=50,000) were dissolved in 70 g of monochlorobenzene to prepare a coating liquid. The coating liquid was applied onto the above-mentioned charge generation layer by a blade coating method to form a charge transport layer having a thickness (after drying) of 19 microns, whereby an electrophotographic photosensitive member was prepared.

The thus prepared photosensitive member was charged by using corona discharge (−5 KV) so as to have an initial potential of $V_0$, left standing in a dark place for 1 sec, and thereafter the surface potential thereof was measured. In order to evaluate the sensitivity, the exposure quantity ($E_{\frac{1}{2}}$, $\mu J/cm^2$) required for decreasing the potential $V_1$ after the dark decay to $\frac{1}{2}$ thereof was measured. The light source used herein was laser light (output: 5 mW, emission wavelength: 780 nm) emitted from a ternary semiconductor comprising gallium/aluminum/arsenic.

The results were as follows:
$V_0$: −716 V
$V_1$: −708 V
$E_{\frac{1}{2}}$: 0.6 $\mu J/cm^2$ The above-mentioned photosensitive member was assembled in a laser beam printer (trade name: LBP-CX, mfd. by Canon K. K.) as an electrophotographic printer equipped with the above-mentioned semiconductor laser using a reversal development system, and subjected to actual image formation.

The image formation conditions used herein were as follows:
surface potential after primary charging: −700 V
surface potential after image exposure: −150 V (exposure quantity: 2.0 $\mu J/cm^2$)
transfer potential: +700 V
polarity of developer: negative
process speed: 50 mm/sec
developing condition (developing bias): −450 V
image exposure scanning system: image scan
exposure prior to the primary charging: 50 lux.sec (whole surface exposure using red light)

The image formation was effected by line-scanning the laser beam corresponding to character and image signals. As a result, good prints were obtained with respect to the characters and images.

Further, when successive image formation of 3,000 sheets was conducted, good prints were stably obtained from the initial stage to 3,000 sheets.

EXAMPLE 12

10 g of oxytitanium phthalocyanine and a solution obtained by dissolving 5 g of a phenoxy resin in 485 g of dioxane were dispersed for 2 hours by means of a ball mill. The thus prepared dispersion was applied onto an aluminum sheet by means of a wire bar and then dried at 80° C. for 2 hours to form a charge generation layer having a thickness of 0.5 micron.

Then, 10 g of the above-mentioned Compound Example No. 24 and 10 g of a bisphenol Z-type polycarbonate resin (weight-average molecular weight=50,000) were dissolved in 70 g of monochlorobenzene to applied onto the above-mentioned charge generation layer by means of a wire bar and then dried at 110° C. for one hour to form a charge transport layer having a thickness of 19 microns, whereby an electrophotographic photosensitive member was prepared.

The thus obtained photosensitive member was evaluated in the same manner as in Example 11. The results were as follows:
$V_0$: −741 V
$V_1$: −719 V
$E_{\frac{1}{2}}$: 0.8 $\mu J/cm^2$

EXAMPLE 13

3 g of 4-(4-dimethylaminophenyl)-2,6-diphenyl-thiapyrilium perchlorate, 5 g of Compound Example No. 18 as a charge-transporting substance, and 5 g of a polyester resin (weight-average molecular weight=49,000) were mixed with 50 g of a solvent comprising toluene and dioxane (1:1) and dispersed for 6 hours by means of a ball mill. The thus prepared dispersion was applied onto an aluminum sheet by means of a wire bar and then dried at 100° C. for 2 hours to form a photosensitive layer having a thickness of 15 microns, whereby an electrophotographic photosensitive member was prepared.

The thus obtained photosensitive member was evaluated in the same manner as in Example 1. The results were as follows:

$V_0$: —702 V
$V_1$: —689 V
$E_{\frac{1}{2}}$: 2.9 lux.sec
(Initial stage)
$V_D$: —700 V
$V_L$: —200
(After copying of 5,000 sheets)
$V_D$: —681 V
$V_L$: —216 V

EXAMPLE 14

An aqueous ammonia solution of casein (comprising 11.2 g of casein, 1 g of 28 % ammonia water, and 222 ml of water) was applied onto an aluminum plate by means of a wire bar to form a primer layer having a thickness of 1 micron (after drying). On the primer layer, a charge transport layer and a charge generation layer were successively formed in the same manner as in Example 10, whereby an electrophotographic photosensitive member was prepared in the same manner as in Example 1 except that the laminate structure was different.

The charging characteristics of the thus obtained photosensitive member were evaluated in the same manner as in Example 1. The results were as follows:
$V_0$: +701 V
$V_1$: +675 V
$E_{\frac{1}{2}}$: 2.8 lux.sec

EXAMPLE 15

A 5 % methanol solution of a soluble nylon (6-66-610-12 quaternary copolymer nylon) was applied onto an aluminum substrate to form a primer layer having a thickness of 0.5 micron (after drying).

Then, 5 of a pigment represented by the following formula:

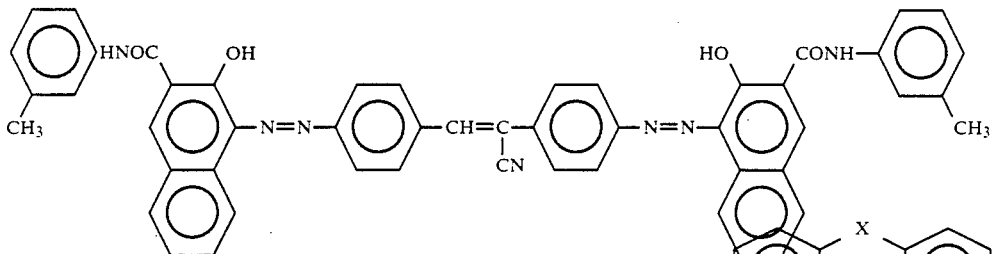

was dispersed in 95 ml of tetrahydrofuran for 20 hours by means of a sand mill to prepare a dispersion.

Separately, 5 g of the above-mentioned Compound Example No. 11 and 10 g of a bisphenol Z-type polycarbonate resin (weight-average molecular weight = 50,000) were dissolved in 30 ml of monochlorobenzene to prepare a solution. The solution was then added to the above-mentioned dispersion, and further dispersed by means of a sand mill for 2 hours, thereby to prepare a coating liquid. The thus prepared coating liquid was applied onto the above-mentioned primer layer by means of a wire bar to form a photosensitive layer having a thickness of 20 microns (after drying), whereby an electrophotographic photosensitive member was prepared.

The electrophotographic characteristics of the thus obtained photosensitive member were evaluated in the same manner as in Example 1. The results were as follows:
$V_0$: —736 V
$V_1$: —709 V
$E_{\frac{1}{2}}$: 3.1 lux.sec

What is claimed is:

1. A photosensitive member for electrophotography, comprising an electroconductive substrate and a photosensitive layer disposed thereon, wherein the photosensitive layer comprises a substituted amino compound having a charge-transporting function and represented by the following general formula (I):

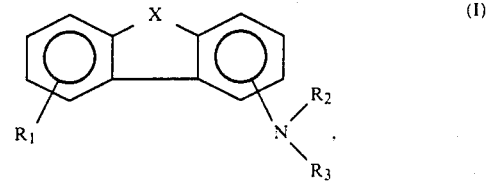

wherein X denotes —O—, —S—, or

$R_1$ denotes a hydrogen atom, alkyl, alkoxyl or halogen atom; and $R_2$, $R_3$ and $R_4$ respectively denote an alkyl, aralkyl, aryl or heterocyclic group.

2. A member according to claim 1, wherein the compound of the general formula (I) is represented by the following general formula (II)

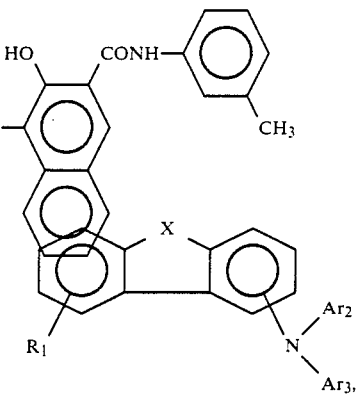

wherein X and $R_1$ are the same as defined above, and $Ar_1$ and $Ar_2$ respectively denote an aryl group.

3. A member according to claim 1 or 2, wherein the photosensitive layer has a laminate structure comprising a charge generation layer and a charge transport layer.

4. A member according to claim 3, which comprises the electroconductive substrate, and the charge generation layer and the charge transport layer in this order on the substrate.

5. A member according to claim 3, which comprises the electroconductive substrate, and the charge transport layer and the charge generation layer in this order on the substrate.

6. A member according to claim 3, wherein the charge transport layer comprises the compound represented by the formula (I) or (II), and an insulating polymer or organic photoconductive polymer.

7. A member according to claim 3, wherein the charge transport layer comprises the compound represented by the formula (I) or (II), an insulating polymer or organic photoconductive polymer, and at least one species selected from the group consisting of a plasticizer, a surface lubricating agent, a potential stabilizing agent, and an anti-oxidizing agent.

8. A member according to claim 3, wherein the charge generation layer comprises an organic charge-generating substance and an insulating resin.

9. A member according to claim 8, wherein the organic charge-generating substance comprises an azo pigment.

10. A member according to claim 1 or 2, which further comprises a primer layer disposed between the electroconductive substrate and photosensitive layer.

11. A member according to claim 1 or 2, which further comprises a protective layer disposed on the photosensitive layer.

* * * * *

UNITED STATES PATENT AND TRADEMARK OFFICE
CERTIFICATE OF CORRECTION

PATENT NO. : 5,049,464

DATED : September 17, 1991

INVENTOR(S) : TETSURO KANEMARU, ET AL.

Page 1 of 3

It is certified that error appears in the above-identified patent and that said Letters Patent is hereby corrected as shown below:

On title page, item

IN [56] REFERENCES CITED

U.S. PATENT DOCUMENTS, "3,857,851  9/1974" should read --3,837,851  9/1974--.

COLUMN 1

Line 30, "a" should read --as--.
Line 37, "can not" should read --cannot--.

COLUMN 2

Line 38, "denotes" should read -- $R_1$ denotes--.

COLUMN 8

Line 13, "such as" should read --as a--.
Line 14, "the" (first occurrence) should be deleted.
Line 20, "polycarbonate" should read --polycarbonate,--.
Line 25, "styrene-maelic" should read --styrene-maleic--.

COLUMN 10

Line 20, "$C_p)_n$" should read --$Cp)_n$--.
Formula A-1, "F" should read --R--.

COLUMN 13

Line 38, "structures;" should read --structures:--.

COLUMN 15

Line 67, "to" should be deleted.

UNITED STATES PATENT AND TRADEMARK OFFICE
CERTIFICATE OF CORRECTION

PATENT NO. : 5,049,464

DATED : September 17, 1991

INVENTOR(S) : TETSURO KANEMARU, ET AL.

It is certified that error appears in the above-identified patent and that said Letters Patent is hereby corrected as shown below:

COLUMN 16

Line 30, "sheet," should read --a sheet,--.

COLUMN 17

Line 68, "mfd" should read --mfd.--.

COLUMN 18

Line 16, "(VL)" should read --($V_L$)-- and "(VD)" should read --($V_D$)--.
Line 18, "VD and VL" should read --$V_D$ and $V_L$--.

COLUMN 19

Line 14, "characteristic" should read --characteristics--.
Line 23, "characteristic" should read --characteristics--.

COLUMN 20

Line 52, "As" should read --As is--.

COLUMN 21

Line 43, "($E_{½}$, µJ/cm$^2$)" should read --($E_{½}$, µJ/cm$^2$)--.

COLUMN 22

Line 41, "to applied" should read --to prepare a coating liquid. The coating liquid was applied--.

UNITED STATES PATENT AND TRADEMARK OFFICE
CERTIFICATE OF CORRECTION

PATENT NO. : 5,049,464
DATED : September 17, 1991
INVENTOR(S) : TETSURO KANEMARU, ET AL.

Page 3 of 3

It is certified that error appears in the above-identified patent and that said Letters Patent is hereby corrected as shown below:

COLUMN 23

Line 34, "5" should read --5 g--.

COLUMN 24

Line 30, "(II)" should read --(II):--.

Lines 45-50, " 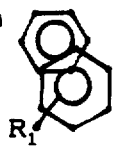 " should read 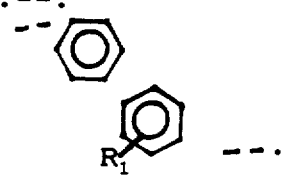 --.

COLUMN 26

Line 9, "and" should read --and the--.

Signed and Sealed this

Ninth Day of March, 1993

Attest:

STEPHEN G. KUNIN

Attesting Officer

Acting Commissioner of Patents and Trademarks